United States Patent [19]

Carlson et al.

[11] Patent Number: 5,532,382
[45] Date of Patent: Jul. 2, 1996

[54] BENZOTHIOPHENES SUBSTITUTED AT THE 3-CARBONYL

[75] Inventors: Donald G. Carlson, Indianapolis; George J. Cullinan, Trafalgar; Kennan J. Fahey; William T. Jackson, both of Indianapolis; Neal W. Roehm, Zionsville; Stephen M. Spaethe, Carmel, all of Ind.

[73] Assignee: Eli Lilly and Company, Indianapolis, Ind.

[21] Appl. No.: 402,683

[22] Filed: Mar. 13, 1995

[51] Int. Cl.⁶ .................... C07D 333/56; C07D 333/64
[52] U.S. Cl. ............................................ 549/57; 549/51
[58] Field of Search .................. 549/51, 57; 514/443, 514/825, 826, 863

[56] References Cited

U.S. PATENT DOCUMENTS

| | | | |
|---|---|---|---|
| 4,133,814 | 1/1979 | Jones et al. | 549/52 |
| 4,380,635 | 4/1983 | Peters | 546/202 |
| 4,418,068 | 11/1983 | Jones | 549/51 |
| 4,863,958 | 9/1989 | Belanger et al. | 514/469 |
| 4,963,580 | 10/1990 | Zambias et al. | 514/443 |
| 5,093,351 | 3/1992 | Batt | 514/415 |

FOREIGN PATENT DOCUMENTS

| | | |
|---|---|---|
| 0416609A2 | 3/1991 | European Pat. Off. . |
| 584952A1 | 3/1994 | European Pat. Off. . |
| 617030A1 | 9/1994 | European Pat. Off. . |

OTHER PUBLICATIONS

Brooks, et al., *Drugs of the Future*, 18(7), 616–618 (1993).

*Primary Examiner*—Richard L. Raymond
*Assistant Examiner*—Deborah Lambkin
*Attorney, Agent, or Firm*—Janelle D. Strode; James J. Sales; David E. Boone

[57] ABSTRACT

Provided are compounds of the formula II

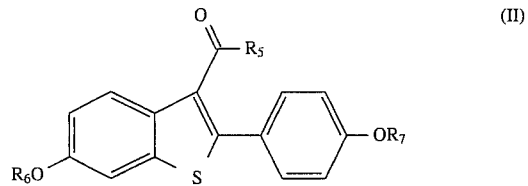

wherein $R_6$ and $R_7$ are independently hydrogen or $C_1$–$C_6$ alkyl;

$R_5$ is naphthyl, substituted nephthyl, or phenyl substituted one to three times with $C_1$–$C_6$ alkoxy, $C_1$–$C_6$ alkyl, phenyl, or hydroxy; with the proviso that if the phenyl is substituted once with hydroxy, it must be further be substituted once or twice with $C_1$–$C_6$ alkoxy, $C_1$–$C_6$ alkyl, phenyl or hydroxy, and pharmaceutically acceptable salts thereof.

4 Claims, No Drawings

BENZOTHIOPHENES SUBSTITUTED AT THE 3-CARBONYL

BACKGROUND OF THE INVENTION

This invention relates to certain benzothiophenes, compositions containing those compounds, and methods of their use.

The enzyme 5-lipoxygenase (5-LO) catalyzes the first step of a biochemical synthesis pathway by which arachidonic acid is converted into leukotrienes. Numerous and extremely potent biological activities have been associated with leukotrienes. Leukotrienes have been implicated as important mediators in a variety of disease states such as asthma, arthritis, psoriasis, ischemia, allergy, adult respiratory distress syndrome (ARDS), and inflammatory bowel disease (IBD).

Considerable efforts have been directed toward the control of leukotriene biosynthesis. Generally, research efforts directed toward the control of leukotriene biosynthesis have been directed toward the discovery of inhibitors of the 5-LO pathway and, in particular, 5-LO specific inhibitors.

In U.K. Patent Application GB 2,196,629 certain ring substnituted-N-hydroxy-N-substituted benzamide and cinnamamide compounds are disclosed as antileukotriene agents. The ring substituent may be a group having the formula (Ra) (Rb) C═CH—where (Ra) (Rb)C═ is an unsaturated aliphatic hydrocarbylene group containing 3 to 19 carbon atoms, a group having the formula $R_3$═C═C— where $R_3$ is a hydrogen atom or a saturated or unsaturated aliphatic hydrocarbyl group containing 1 to 18 carbon atoms or a group having the formula $R_4$—S— where $R_4$ is an aliphatic hydrocarbyl group containing 1 to 20 carbon atoms. The N-substituent may be a $C_1$–$C_6$ alkyl group, a $C_3$–$C_7$ cycloalkyl group or a substituted or unsubstituted aryl group.

In European Patent Application 0196184 certain aryl compounds are disclosed which include, among many others, certain cinnamohydroxamic acid analogs and certain N-hydroxyureas in Examples 81–91. Certain urea based or urea containing compounds that are said to inihibit lipoxygenase are disclosed in EPO 0292699; EPO 0279281; and EPO 0279263. These references contain a recognition of the importance of 3-[2-(halo-phenylthio)phenyl]prop-2-enyl substituted on a urea skeleton.

In WO 90/12008 certain unsubstituted and substituted phenyl, naphthyl and thienyl N-hydroxy ureas are disclosed as inhibitors of 5- and 12-lipoxgenase. The preparation and biological activity for a number of such derivatives is disclosed. The present invention is directed to the discovery that a select group of N-hydroxy-N-[3-[2-[4-halophenylthio)phenyl]-prop-2-enyl] ureas are extremely potent 5-LO inhibitors.

Another important compound of the thienyl N-hydroxyurea class is (I)-N-(1-benzo[B]thien-2-ylethyl)-N-hydroxyurea, i.e., Zileuton. The synthesis of Zileuton is described in U.S. Pat. No. 4,873,259 and its experimental pharmacology and clinical evaluation are reviewed in "Drugs of the Future 993", 18(7), P. 616–618.

The compounds of the present invention, as defined herein, are inhibitors of 5-LO and have useful medical prophylactic and therapeutic properties.

SUMMARY OF THE INVENTION

This invention provides compounds of the formula II

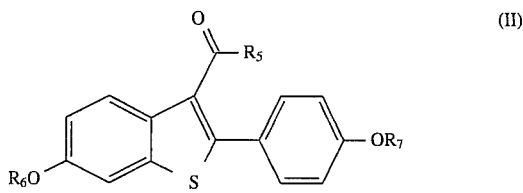

wherein $R_6$ and $R_7$ are independently hydrogen or $C_1$–$C_6$ alkyl;

$R_5$ is naphthyl, substituted naphthyl, or phenyl substituted one to three times with $C_1$–$C_6$alkoxy, $C_1$–$C_6$ alkyl, phenyl, or hydroxy; with the proviso that if the phenyl is substituted once with hydroxy, it must further be substituted once or twice with $C_1$–$C_6$ alkoxy, $C_1$–$C_6$ alkyl, phenyl or hydroxy, and pharmaceutically acceptable salts thereof.

Also provided are methods of inhibiting a 5-lipoxygenase and leukeotrienes.

DETAILED DESCRIPTION OF THE INVENTION

The current invention concerns the discovery that a group of benzothiophenes, those of formula I, below, and II, are useful for inhibiting 5-lipoxygenase

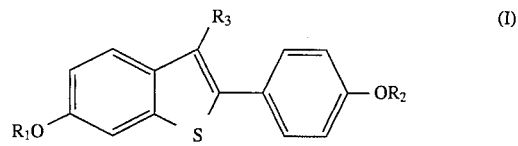

wherein $R_1$ and $R_2$ are independently hydrogen or $C_1$–$C_6$ alkyl;

$R_3$ is hydrogen, or a group of the formula

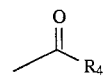

wherein $R_4$ is phenyl, substituted phenyl naphthyl or substituted naphthyl, with the proviso that when $R_1$ and $R_2$ are both $C_1$–$C_6$ alkyl, $R_3$ is not hydrogen; and pharmaceutically acceptable salts thereof.

Further novel benzothiophenes of formula II are provided.

The therapeutic and prophylactic treatments provided by this invention are practiced by administering to a human in need thereof a dose of a compound of formula I or II, or a pharmaceutically acceptable salt or solvate thereof, that is effective to inhibit 5-lipoxygenase, or a physiological disorder associated with an excess of leukotrienes.

The term "inhibit" includes its generally accepted meaning which includes prohibiting, preventing, restraining, and slowing, stopping or reversing progression, severity or a resultant symptom. As such, the present method includes both medical therapeutic and/or prophylactic administration, as appropriate.

The term "substituted phenyl" and "substituted napthyl" includes the particular aryl group substituted once to three times with $C_1$–$C_6$ alkyl, $C_1$–$C_4$ alkoxy, hydroxy, nitro, chloro, fluoro, or tri(chloro or fluoro)methyl.

A variety of physiologic functions have been associated with leukotrienes. As such, the compounds of formula I and II are believed to have the ability to treat in mammals a variety of disorders associated with an excess of leukotrienes such as asthma and allergic diseases, (including rhinitis and hayfever), eczema, bronchitis, inflammatory bowel disease, psoriasis, shock, ischemia, adult respiratory distress syndrome and arthritis. Therefore, the present invention also provides methods of inhibiting the above disorders at the rates set out, for inhibiting the 5-lipoxygenase conversion to leukotrienes, by administering to a mammal in need of 5-lipoxygenase inhibition, an asthma, allergic disease, eczema, bronchitis, inflammatory bowel disease, psoriasis, shock, ischemia, adult respiratory distress syndrome or arthritis relieving dose of a compound of the present invention.

Recent clinical studies have supported a role for a leukotriene antagonist in the treatment of asthma (Cloud et al. J. Allergy Clin. Immunol., 79 256 (1987)) thus providing further evidence of the importance of leukotrienes in clinical asthma. Further evidence obtained over the past few years has shown the presence of leukotrienes in sputum of patients with chronic bronchitis (Turnbull, et al., *Lancet* II, 526 (1977) and cystic fibrosis (Cromwell, et al., *Lancet* II, 164 1981)), suggesting a role of leukotrienes in the pathology of those diseases as well. Furthermore, Lewis and colleagues (*Int. J. Immunopharmacology,* 4, 85 (1982)) have detected material in rheumatoid synovial fluid that reacts antigenically with antibody to $LTD_4$. This may hallmark the existence of leukotriene permeability factors that, together with LTB4, augment the inflammatory process in the diseased joints. Therefore, the compounds described in this invention should also alleviate some of the symptoms of chronic bronchitis and cystic fibrosis and possibly rheumatoid arthritis by virtue of their ability to inhibit leukotrienes. The compounds are also useful for inhibiting the cardiovascular effects of leukotrienes thereby rendering them useful for treating conditions such as shock and ischemic heart disease. Evidence that leukotrienes are involved in cardiovascular conditions and in shock syndromes is provided by the work of Cook et al., (*J. Pharmacol. Exp. Ther.,* 235, 470–474 (1985)); Eimerl et al., (*Am. J. Physiol.,* 251 H700–H709 (1986)); Etemadi et al., (*Circ. Shock,* 22, 55–63 (1987)); and Hock and Lefer, (*Circ. Shock,* 17, 263–272 (1985)).

Generally, at least one compound of formula I or II is formulated with common excipients, diluents or carriers, and compressed into tablets, or formulated as elixirs or solutions for convenient oral administration, or administered by the intramuscular or intravenous routes. The compounds can be administered transdermally, and may be formulated as sustained release dosage forms, aerosol forms, and the like.

The compounds used in the methods of the current invention can be made according to established procedures, such as those detailed in U.S. Pat. Nos. 4,133,814, 4,418,068, and 4,380,635, all of which are incorporated by reference herein. The following scheme and examples are provided to illustrate preparation of the compounds.

Scheme I

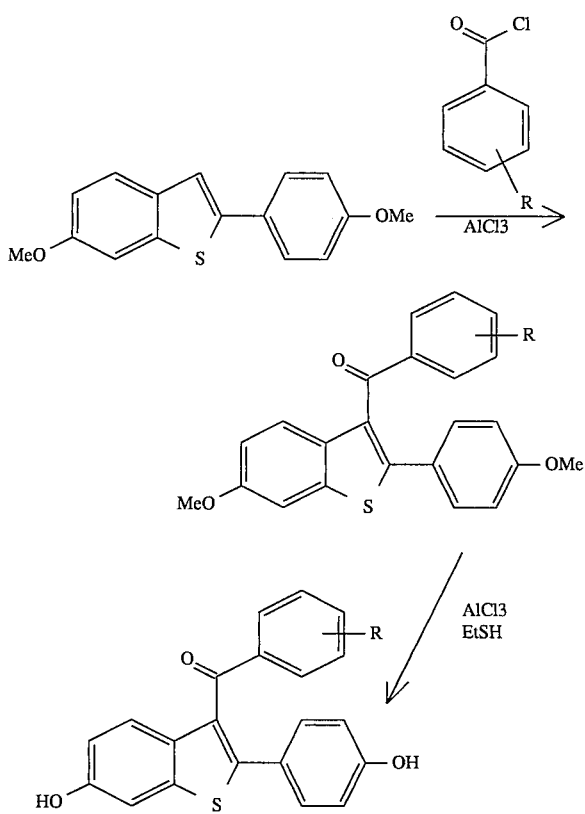

The above Scheme I can be carried out as a two-step process or a one-pot process. The following describes the one pot process.

EXAMPLE 1

6-hydroxyphenyl-2-(p-hydroxyphenyl)-(benzo(B)thien-3-yl)(p-phenyl)phenyl methanone To 100 mL of methylene chloride was added 2 drops DMF, 3 g (15 mmol) of 4-phenyl benzoic acid, and 15 mls of $SOCl_2$. The mixture was heated to reflux for 16 hours then reduced to dryness. To the resulting acid chloride was added 4 g (15 mmol) of 6-methoxy-2-(4-methoxyphenyl)benzo[B] thiophene and 600 mL of methylene chloride followed by 14 g (105 mmol) of $AlC_3$ over 5 mins. This mixture was then heated to reflux for 45 minutes, cooled to room temperature, and 15 mLs (203 mmol) of EtSH was added. The mixture was again heated to reflux for 35 minutes, cooled to room temperature and quenched by careful addition of 50 mL MeOH followed by 100 mL of $H_2O$. After the mixture turned yellow, the mixture was partitioned. The organic layer was dried over $Na_2SO_4$ and reduced to dryness. The product was then purified over silica using a 15 to 30% gradient of EtOAc:hexanes as the eluent. The product was then crystallized from hexanes to yield 300 mgs (11% yield) of the desired product as a yellow solid. $^1H$ NMR consistent with structure; FD+MS=422; EA (Theory/Found) C 76.76/75.94, H 4.29/4.83.

EXAMPLE 2

6-hydroxyphenyl-2-(p-hydroxyphenyl)-(benzo(B)thien-3-yl) (α-naphyl)methanone

As in Example 1, but using α-naphthoyl chloride as the starting material. 700 mgs (48% yield) of product isolated as

EXAMPLE 3

6-hydroxyphenl-2-(p-hydroxyphenyl)-
(benzo(B)thien-3-yl) (β-napthyl)methanone

As in Example 1, but using β-naphthoyl chloride as the starting material. 810 mgs (55% yield of product isolated as a bright orange solid. ¹H NMR consistent with structure; FD+MS=396; EA (Theory/Found) C 75.74/75.76, H 4.07/4.36.

The following is a description of Scheme 1 as a two step synthesis.

EXAMPLE 4

6-hydroxyphenyl-
2-(p-hydroxyphenyl)-(benzo(B)thien-3-yl)
(p-phenyl)phenyl methanone (a) To 800 mls of menhylene chloride at 0 degrees C. was added 16.6 g (76.6 mmol) of p-phenyl benzoyl chloride, 13.8 g (51.1 mmol ) of 6-methoxy-2-(4-methoxyphenyl-)benzo[B] thiophene, and then 20.43 g (153 mmol) AlCl₃ was added portion wise over 20 minutes. The mixture was stirred at 0 degrees for 2 hours then poured over ice iand diluted with brine. The layers were separated and the organic layer was washed ×3 ×350 mls with saturated sodium bicarbonate solution followed by ×2 ×400 mls with de-ionized water. The organic layer was dried on sodium sulfate and reduced to dryness. The crude product was purified using HPLC and a 5 to 25% gradient of EtOAc:hexanes as the eluent to provide 14.5 g (63% yield) of product as a yellow solid. ¹H NMR consistent with structure.

(b) To 100 mls of methylene chloride at 0 deg C. was added 6 g (13.3 mmol) of the compound from step 4(a), 8.9 g (66.7 mmol) AlCl₃ was added portion wise over 20 minutes, and then 10 mls (35 mmol) of EtSH was added all at once. This mixture was heated to reflux for 2.5 hours and then allowed to cool back to room temperature. The reaction was then quenched by carefully pouring over ice, adding 50 mls THF, then diluting with brine. The layers were separated and the organic layer was washed ×3 ×350 mls with saturated sodium bicarbonate solution followed by ×1 ×506 mls de-ionized water. The organic layer was then dried on sodium sulfate and reduced to dryness. The crude produce was purified on silica using 15 to 30% EtOAc:hexanes gradient as the eluent to yield 3.7 g of the desired product as a yellow solid. ¹H NMR consistent with structure; FD+MS=422.

EXAMPLE 5

6-hydroxyphenyl-2-(p-hydroxyphenyl)-
(benzo(B)thien-3-yl)(α-napthyl)methanone (a) As in Example 4a, but using α-naphthoyl chloride as the starting material. 10.6 g (68% yield) of product isolated as a yellow solid. ¹H NMR consistent with structure; FD+MS=424.

(b) As in example (4b), but using the product from step 5(a) as the starting material. 4.8 g (87% yield) of product isolated as a yellow solid. ¹H NMR consistent with structure; FD+MS=396.

EXAMPLE 6

6-hydroxypheny-2-(p-hydroxyphenyl)-
(benzo(B)thien-3-yl)(α-napthyl)methanone (a) As in example 4 a, but using β-naphthoyl chloride as the starting material. 9.2 g (59% yield) of product isolated as a yellow solid. ¹H NMR consistent with structure; FD+MS=424.

(b) As in example 4(b), bun using the product from step 6 (a) as the starting material. 5.3 g (97% yield) of product isolated as a yellow solid. ¹H NMR consistent with structure; FD+MS=396.

EXAMPLE 7

(a) 6-methoxyphenyl-2.-(p-methoxyphenyl)-
(benzo(b)thien-3-yl
4-hydroxy-3,5-dimethoxyphenyl) methanone (b) 6-methoxyphenyl-2-(p-methoxyphenyl)-
(benzo(b)thien-3-yl
(3,4,5-trimenhoxyphenyl)methanone (c) As in example 4(a) but using 3,4,5-tri-methoxy benzoyl chloride as the starting material. Both products were isolated from a silica column using 20 to 40% EtOAc:hexanes as the eluent.

Product (a) was isolated as a yellow solid, with a yield of 1.8 g (38% yield ¹H NMR consistent with structure; FD+MS=450; E.A (Theory/Found) C 66.65/66.86, H;. 4.92/5.21. Product (b) was isolated as a yellow solid with a yield of 900 mgs (19% yield) 1H NMR consistent with structure; FD+MS=464; EA (Theory/Found) C 67.22/67.48H 5.21/5.26.

EXAMPLE 8

6-hydroxyphenyl-2-(p-hydroxyphenyl)-
(benzo(b)thien-3-yl (p-t-butylohenyl)methanone (a) As in example 4a, but using 4-t-butyl benzoyl chloride as the starting material. 3.1 g (97% yield) of product isolated as a thick yellow oil. ¹H NMR consistent with structure; FD+MS=430; EA (Theory/Found) C 75.32/75.49, H 6.09/6.2.

(b) As in example 4 (b), but using the product from step 8 (a) as the starting material, 550 mgs (59 yield) of product isolated as a yellow solid. ¹H NMR consistent with structure; FD+MS=402. EA (Theory/Found) C 74.6C 74.90, H 5.51/5.80.

EXAMPLE 9

6-hydroxyphenyl-2-(p-hydroxyphenyl)-(benzo(B)
thienyl-3-yl(p-methylphenyl)methanone (a) As in example 4, but using 4-methyi benzoyl chloride as the starting material. 1.9 g (65% yield ) of product isolated as a yellow solid. ¹H NMR consistent with structure;

FD+MS=388; EA (Theory/Found) C 74.20/73.85, H 5.19/5.20.

(b) As in example 4 (b), but using the product from Step 9 (a) as the starting material. 700 mgs (75% yield) of product isolated as a yellow solid. ¹H NMR consistent with structure; FD+MS:=360. EA (Theory/Found) C 73.31/73.57, H 4.47/4.58.

EXAMPLE 10

6-hydroxyphenyl-2-(p-hydroxy phenyl)-(benzo(B)thienyl-3-yl (m-methylphenyl)methanone (a) As in example 4(a), but using m-methyl benzoyl chloride as the starting material. 4.7 g (60% yield) of product isolated as a yellow gum. $^1$H NMR consistent with structure; FD+MS=388; EA (Theory/Found) C 74.20/14.46, H 5.19/5.33.

(b) As in example 4(b), but using the product from step 10(a) as the starting material. 190 mgs (20% yield) of product isolated as a yellow solid. $^1$H NMR consistent with structure. EA (Theory/Found) C 73.31/73.08, H 4.47/4.70.

EXAMPLE 11

6-hydroxyphenyl-2-(p-hydroxyphenyl)-(benzo(B)thien-3-yl(m-hydroxy phenyl)methanone (a) As in example 4(a), but using m-me hoxy benzoyl chloride as the starting material. 2.5 g (84% yield) of product isolated as a yellow solid. 1H NMR consistent with structure; FD+MS=404.

(b) As in example 4(b), but using the product of step 11 (a) as the starting material. 400 mgs yield) of product isolated as a yellow solid. $^1$H NMR consistent with structure; FD+MS=362. EA (Theory/Found) C 69.60/68.61, H 3.89/4.44.

The compounds used in the methods of this invention may form pharmaceutically acceptable salts with a wide variety of organic and inorganic bases and include the physiologically acceptable salts which are often used in pharmaceutical chemistry. Such salts are also part of this invention. Bases commonly used for formation of salts include ammonium hydroxide and alkali and alkaline earth metal hydroxides, carbonates, as well as aliphatic and primary, secondary and tertiary amines, aliphatic diamines. Bases especially useful in the preparation of addition salts include ammonium hydroxide, potassium carbonate, methylamine, diethylamine, ethylene diamine and cyclohexylamine.

The pharmaceutically acceptable salts generally have enhanced solubility characteristics compared to the compound from which they are derived, and thus are often more amenable to formulation as liquids or emulsions.

Pharmaceutical formulations can be prepared by procedures known in the art. For example, the compounds can be formulated with common excipients, diluents, or carriers, and formed into tablets, capsules, suspensions, powders, and the like. Examples of excipients, diluents, and carriers that are suitable for such formulations include the following: fillers and extenders such as starch, sugars, mannitol, and silicic derivatives; binding agents such as carboxymethyl cellulose and other cellulose derivatives, alginates, gelatin, and polyvinyl pyrroidone; moisturizing agents such as glycerol; disintegrating agents such as calcium carbonate and sodium bicarbonate; agents for retarding dissolution such as paraffin; resorption accelerators such as quaternary ammoniun compounds; surface active agents such as cenyl alcohol, glycerol monostearate; adsorptive carriers such as kaolin and bentonite; and lubricants such as talc, calcium and magnesium stearate, and solid polyethyl glycols.

The compounds can also be formulated as elixirs or solutions for convenient oral administration or as solutions appropriate for parenteral administration, for instance by intramuscular, subcutaneous or intravenous routes. Additionally, the compounds are well suited to formulation as sustained release dosage forms and the like. Also, the compounds may be formulated for aerosol use or nasal inhalation. The formulations can be so constituted that they release the active ingredient only or preferably in a particular part of the intestinal tract, possibly over a period of time. The coatings, envelopes, and protective matrices may be made, for example, from polymeric substances or waxes.

The particular dosage of a compound of formula I or II required to inhibit 5-lipoxygenase, or no carry out any of the methods disclosed herein, according to this invention, will depend upon the severity of the condition, the route of administration, and related factors that will be decided by the attending physician. Generally, accepted and effective daily doses will be from about 0.1 to about 1000 mg/day, and more typically from about 50 to about 200 mg/day. Such dosages will be administered to a subject in need thereof from once to about three times each day, or more often as needed to effectively inhibit 5-lipoxygenase or its effects, or any other use disclosed herein.

Formulations

In the formulations which follow, "Active ingredient" means a compound of formula I or II.

Formulation 1: Gelatin Capsules Hard gelatin capsules are prepared using the following:

| Ingredient | Quantity (mg/capsule) |
| --- | --- |
| Active ingredient | 0.1–1000 |
| Starch, NF | 0–650 |
| Starch flowable powder | 0–650 |
| Silicone fluid 350 centistokes | 0–15 |

The ingredients are blended, passed through a No. 45 mesh U.S. sieve, and filled into hard gelatin capsules.

Examples of specific capsule formulations that may be made include those shown below:

Formulation 2: Capsule

| Ingredient | Quantity (mg/capsule) |
| --- | --- |
| Active Ingredient | 1 |
| Starch, NF | 112 |
| Starch flowable powder | 225.3 |
| Silicone fluid 350 centistokes | 1.7 |

Formulation 3: Capsule

| Ingredient | Quantity (mg/capsule) |
| --- | --- |
| Active Ingredient | 5 |
| Starch, NF | 108 |
| Starch flowable powder | 225.3 |
| Silicone fluid 350 centistokes | 1.7 |

Formulation 4: Capsule

| Ingredient | Quantity (mg/capsule) |
| --- | --- |
| Active Ingredient | 10 |
| Starch, NF | 103 |
| Starch flowable powder | 225.3 |
| Silicone fluid 350 centistokes | 1.7 |

Formulation 5: Capsule

| Ingredient | Quantity (mg/capsule) |
| --- | --- |
| Active Ingredient | 50 |
| Starch, NF | 150 |
| Starch flowable powder | 397 |
| Silicone fluid 350 centistokes | 3.0 |

The specific formulations above may be changed in compliance with the reasonable variations provided.

A tablet formulation is prepared using the ingredients below:

Formulation 6: Tablets

| Ingredient | Quantity (mg/tablet) |
| --- | --- |
| Active ingredient | 0.1–1000 |
| Cellulose, microcrystalline | 0–650 |
| Silicon dioxide, fumed | 0–650 |
| Stearate acid | 0–15 |

The components are blended and compressed o form tablets.

Alternatively, tablets each containing 0.1–1000 mg of active ingredient are made up as follows:

Formulation 7: Tablets

| Ingredient | Quantity (mg/tablet) |
| --- | --- |
| Active ingredient | 0.1–1000 |
| Starch | 45 |
| Cellulose, microcrystalline | 35 |
| Polyvinylpyrrolidone (as 10% solution in water) | 4 |
| Sodium carboxymethyl cellulose | 4.5 |
| Magnesium stearate | 0.5 |
| Talc | 1 |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced art dried at 500°–60° C. and passed through a No. 18 mesh U.S. sieve. The sodium carboxymethyl starch, magnesium stearate, and talc, previously passed through a No. 60 U.S. sieve, are then added to the granules which, after mixing, are compressed on a tablet machine to yield tablets.

Suspensions each containing 0.1–1000 mg of medicament per 5 mL dose are made as follows:

Formulation 8: Suspensions

| Ingredient | Quantity (mg/5 ml) |
| --- | --- |
| Active ingredient | 0.1–1000 mg |
| Sodium carboxymethyl cellulose | 50 mg |
| Syrup | 1.25 mg |
| Benzoic acid solution | 0.10 mL |
| Flavor | q.v. |
| Color | q.v. |
| Purified water to | 5 mL |

The active ingredient is passed through a No. 45 mesh U.S. sieve and mixed with the sodium carboxymethyl cellulose and syrup to form a smooth paste. The benzoic acid solution, flavor, and color are diluted with some of the water and added, with stirring. Sufficient water is then added to produce the required volume.

EXAMPLE 9

| Ingredient | Quantity (mg/5 ml) |
| --- | --- |
| Active ingredient | 10 mg |
| Ethanol | 50 mg |
| Dichlorodifluoromethane (Propellant 12) | 658 mg |
| Dichlorotetrafluoroethane (Propellant 114) | 282 mg |

The active ingredient is dissolved in the ethanol. The concentrate is filled into extruded aluminum cans for inhalation aerosols. The cans are degassed with propellant 12 and sealed with an appropriate metered dose valve. The volume of product expelled per actuation is 50 to 100 µl equivalent to 0.5–1 mg active ingredient.

EXAMPLE 10

| Aerosol | mg/ml |
| --- | --- |
| Active ingredient | 0.2 |
| Sorbitan trioleate | 0.27 |
| Trichlorofluoromethane | 70.0 |
| Dichloridifluoromethane | 280.0 |
| Dichlorotetrafluoroethane | 1094.0 |

Test Procedures

The following assays indicate the utility of the compounds.

5-lipoxgenase (5-LPO) Assay

To determine the effect of compounds on 5-lipoxygenase activity, peripheral blood neutrophils are separated by density centrifugation as described (Marder et al., *Prostaglandins Leukot. and Essent. Fatty Acids* 46, 265–270, 1992) and the cytosolic 5-lipoxygenase is prepared from isolated neutrophils according to a modification of Carter al., (*J. Pharmacol. Exp. Ther.* 256, 929–337 (1991)). Briefly, neutrophils are washed twice in, buffer (in millimolar: PIPES, 10; BES, 10; and EDTA, 1; pH 6.8) and diluted to $2.5 \times 10^7$ cells/ml. Cells are disrupted with sonication and the cytosolic fraction obtained by centrifugation at 20,000×g for 20 min. at 4° C. The resultant supernatant containing the cytosolic 5-lipoxygenase activity is stored frozen at −70° C. prior no use. Compounds are evaluated for 5-lipoxygenase inhibitor activity. Varying concentration of compounds in 200 ml aliquots containing 50 ml of human 20,000×g supetnatant in assay buffer (in millimolar: PIPES, 10; BES, 10; EDTA, 1; NaCl, 100; ATP, 1.56; and $CaCl_2$, 2.5; pH 6.8) containing 3.0 mM AA are used. The reaction proceeds for 5 minutes at 37° C. and is terminated upon the addition of 50 ml EDTA (250 mM). The percent inhibition of leukotriene $B_4$ is determined for each concentration of test compound as compared to vehicle (containing no compound) control. The concentration representing 50% inhibition ($IC_{50}$) is determined by standard mathematical techniques. Leukotriene $B_4$ is determined by EIA. EIA reagents were purchased from Gaymen Chemical Co. (Ann Arbor, Mich.) and used according to the assay procedures as outlined therein.

cPLA2 Enzymatic Activity Assay

The substrate, sonicated liposomes containing 1-palmitoyl-2-[$^{14}$C]archachidonoyl-sn-glycero-3-phosphocholine ([$^{14}$C]PC, 55 mCi/mmol from NEN Research Products) and sn-1,2-dioleoylglycerol (DG, Avanti Polar Lipids, Birmingham, Ala.) at a molar ratio of 2:1, are prepared a follows.

[$^{14}$C]PC (20 nmol, 1×10$^6$ dpm, 50 uCi/ml in toluene/ethanol) and DG (10 nmol, 100 ug/ml in chloroform) are dried under nitrogen. The lipids are dispersed in 1 ml of 150 mM NaCl, 50 mM Hepes, pH 7.5 (assay buffer) by sonication at 4° C., with Microson probesonicator (Heat Systems Ultrasonics) for 4×15 seconds, with 45 second intervals. Bovine serum albumin (essentially fatty acid free, from a 100 mg/ml stock in water, Sigma) is added for cPLA$_2$ activity are incubated with 50 µl liposomes (0.5 to a final concentration of 4 mg/ml. Samples to be assayed nmol[$^{14}$C] PC, 50,000 dpm containing 0.25 nmol of DG) in a total volume of 0.2 ml of assay buffer containing 1 mM CaCl$_2$ and 1 mM 2-ME. Incubations are carried out at 37° C. for 15 minutes and terminated by adding 2 ml of Dole's reagent (2-propanol/heptane/0.5M sulfuric acid, 40:10 :1 containing 10 ug/ml of stearic acid). After mixing, 1.2 ml of heptane and 1 ml of water are added. The mixtures are briefly vortexed and the upper phase transferred to tubes containing 2 ml of heptane and 150 mg of Bio-Sil (Bio-Rad Laboratories) activated at 130° C. before use. The tubes are thoroughly vortexed and centrifuged (1000×g for 5 minutes). The supernatants are decanted into scintillatioi vials. After addition of 10 ml of a liquid scintillation cocktail (Ready Protein+, Beckman) radioactivity is counted, using a Beckman liquid scintillation counter Model LS 7000. High radioactive counts correlate with enzymatic activity. The chromogenic cPLA2 enzyme assay used is analogous to Reynolds et al., *Analytical Biochemistry*, 217, 25–32 (1994).
Inhibition of Eicosanoid Production by Plasma-depleted Blood.

Compounds are evaluated for their ability to inhibit production of leukotriene B$_4$ (LTB$_4$) and thromboxane B$_2$ (TXB$_2$) upon stimulation of human plasma-depleted blood with formyl-methionyl-leucyl-phenylalanine (FMLP) and thrombin. LTB$_4$ is produced by neutrophils and TXB$_2$ by platelets stimulated at their respective receptors with FMLP and thrombin. The assay is carried out in 1 ml deep well polypropylene 96-well plates (Beckman). For the test, ten ml of blood is collected in EDTA at a final concentration of 1.5 mg/ml. Then, 40 ml glucose phosphate buffer containing 0.1% gelatin is added and the suspension centrifuged at 900 g for 10 minutes at room temperature. The supernatant is discarded and the cells washed once with 50 ml buffer before resuspending them in 50 ml Krebs-Ringers-Henseleit Buffer containing 0.1% gelatin, 1 mM CaC$_2$, 1.1 mM MgCl$_2$ (KRH buffer). Working solutions of test compounds are made by dissolving the material in DMSO at 10 mM and diluting with appropriate amounts of KRH buffer. An agonist solution is made containing 1 µM FMLP (sigma) and 10 units/ml of thrombin in KRH buffer (Enzyme Research Labs). The blood cell suspension is first warmed to 37° C. for 5 minutes and then mixed with cytochalasin B (sigma) at a final concentration of 2 µg/ml. In each well 200 µl of the compound solution is incubated with 250 µl of the blood cell, cytochalasin B suspension at 37° C. for 10 min. Stimulation of eicosanoid production is begun by adding 50 µl of the agonist solution. The mixture is then incubated for 2 min. before stopping the reaction by adding 50 µl of a solution containing 275 mM EDTA, 110 µM indomethacin (sigma) and 110 µM of the 5-lipoxygenase inhibitor, N-hydroxy-N-[3-[2-(2propynylthio)phenyl]-2-propenyl]urea. Subsequently, the plate is centrifuged and an aliquot of the supernatant fluid removed for analysis of the eicosanoid content. The amount of LTB$_4$ and TXB$_2$ produced is determined by the use of a competetive enzyme immunoassay using commercial reagents from Cayman Chemical.

MCII MAST CELL LTC4 ASSAY

This assay measures the production of LTC4 by the cytokine dependent mast cell line MCII, stimulated by cross linking the high affinity Fc receptor for IgE (Fc$_e$R1).

The bone marrow derived, cytokine dependent mouse mast cell line MCII (Lilly Research Laboratories( is maintained in log phase growth in complete Dulbecco's' Modified Eagles Medium (GIBCO BRL) supplemented with fetal bovine serum (Hyclone), gentamicin, penicillin and streptomycin (GIBCO BRL) and using concanavalin A (ICN ImmunoBiologicals) induced culture supernatants from the mouse helper T cell clone D10.G4 (ATCC TIB 224) as a source of mast cell growth factors. The MCII cells are passively sensitized with mouse monoclonal IgE by incubation with an appropriate dilution of IgEL b4 (ATCC TIB 141) antibody ascites at 37° C. for 60 minutes and then washed with Hank's Balanced Salt Solution (GIBCO BRL) to remove unbound IgE. The sensitized cells are then preincubatea with drug in complete media for 10 minutes at 37° C. in 96 well polypropylene plates (Costar). Each drug concentration is tested in triplicate at half log dilutions The drug vehicle is dimethyl sulfoxide which is present at final concentration of 0.32% in all wells.

Following preincubation with drug the cells are stimulated by addition of an appropriate dilution of rat anti-mouse IgE monoclonal antibody ascites EM95 (Robert Coffman, DNAX Research Institute) to cross ink Fc$_{68}$ R1 to which IgE has bound. There are 40,000 MCII cells per well in a final volume of 200 µl complete medium. The stimulated cells are incubated at 37° C. for 10 minutes and then LTC4 production is stopped by addition of 25 µl 180 mM EDTA to chelate extracellular Ca$^{++}$.

The amount of LTC4 oroduced is determined in a competitive enzyme immunoassay (EIA) using commercial reagents purchased from Cayman Chemical Co. In the EIA, free LTC4 in the sample competes with enzyme conjugated LTC4 for binding to immobilized anti-LTC4 antibody. The enzyme conjugated to LTC4 is acetylcholinesterase and Elman's reagent is the substrate for the enzyme. The concentration of LTC4 in the unknown sample is determined using a 4-parameter quadratic analysis of a standard curve generated by measuring the optical density resulting from the addition of known amounts of LTC4 to the EIA. The LTC4 capture antibody has a 46% cross reaction with LTD4 and 2% with LTE4.

The positive control on each plate is stimulated MCII cells with dimethyl sulfoxide vehicle alone and the negative control is the same reaction mixture without cells. The background negative control value is subtracted from experimental and positive control values and the data are reported as percent of positive control. When the cells are not sensitized with IgE or in the absence of stimulation with rat anti-mouse IgE monoclonal antibody EM95, the production of LTC4 is below the limit of EIA detection at this sample volume.

MCII MAST CELL TOXICITY ASSAY

This toxicity assay is run in parallel with the MCII mast cell LTC4 assay and serves as an indicator of compound effects on the viability and metabolic activity of the MCII cells. This "toxicity" assay is based on the ability of dehydrogenase enzymes present in viable metabolically active cells to bioreduce the tetrazolium salt XTT yielding a colored, water soluble formazan product. (see, Roehm et al.) An improved colorimetric assay for cell proliferation and viability utilizing the tetrazolium salt XTT. *J. Immunol. Methods* 142:257–65 (1991).

A duplicate polystyrene 96-well tissue culture plate (Costar) is set up with sensitized MCII cells, EM95 ascites, media and dilutions of the test compound as described above. The complete media is supplemented with concanavalin A induced culture supernatants from the mouse helper T cell clone D10.G4, as a source of mast cell growth factors.

Wells of the toxicity assay Elate are pulsed with 25 µl XTT (Sigma) plus phenazine methosulfate (Aldrich) giving a final concentration of 0.2 mg/ml XTT and 25 µM phenazine methosulfate. The plates are incubated at 37° C. in 10% $CO_2$ for 4–12 hours and then production of the XTT formazan product determined by measuring the optical density of the wells at a wavelength of 450 nm. The positive control on each plate is stimulated MCII cells with dimethyl sulfoxide vehicle alone and the negative control is the same reaction mixture without cells. The background negative control value is subtracted from experimental and positive control values and the data are reported as percent of positive control.

The results of the Assays are provided in the following Tables. (The results are in $IC_{50}$ µM). (Compound A is a compound of formula II where $R_6$ and $R_7$ are hydrogen, and $R_5$ is phenyl. Compound B is a compound of formula I where $R_1$, $R_2$ and $R_3$ are hydrogen. Compound C is a compound of formula II wherein $R_6$ and $R_7$ are methyl, and $R_5$ is p-methoxyphenyl. Compound D is a compound of formula II wherein $R_1$ and $R_2$ are hydrogen, and $R_5$ is p-hydroxyphenyl. )

TABLE 1

5-LPO Assay

| Compound | $IC_{50}$ |
|---|---|
| Example 2 | 1.7 ± 0.9 (n = 3) |
| Example 3 | 1.0 ± 0.5 (n = 3) |
| Compound B | 0.2 ± 0.007 (n = 4) |
| Compound C | >10 (n = 4) |
| Zileuton | 1.3 ± 0.9 (n = 3) |

TABLE 2

C-PLA2 Enzyme

| Compound | C14PC/DA6 | Chromogenic |
|---|---|---|
| Compound A | 7.3 ± 0.5 (n = 3) | — |
| Compound B | 7 ± 0.8 (n = 3) | >200 (n = 1) |
| Example 2 | 4.8 ± 1.6 (n = 3) | >200 (n = 1) |
| Example 3 | 2.3 ± 0.6 (n = 3) | 122 (n = 1) |
| Example 1 | <1.2 (n = 2) | 146 (n = 1) |

TABLE 3

MCII Mast Cell

| Compound | $LTC_4$ | Toxicity |
|---|---|---|
| Compound A | 7.1 ± 0.5 (n = 2) | 0.3 (n = 1) |
| Compound B | 0.7 (n = 2) | <10 (n = 1) |
| Example 2 | 0.5 ± 0.2 (n = 4) | >10 (n = 3) |
| Example 3 | 3.9 ± 1.8 (n = 8) | >10 (n = 16) |
| Example 1 | 4.4 | >10 |

TABLE 3-continued

MCII Mast Cell

| Compound | $LTC_4$ | Toxicity |
|---|---|---|
|  | (n = 2) | (n = 1) |
| Compound C | 6.7 ± 3.0 (n = 4) |  |
| Example 11 | 2.7 |  |
| Example 10 | 1.1 ± 0.2 (n = 3) |  |
| Example 8 | 3.5 ± 2.1 (n = 3) |  |
| Example 9 | 0.8 ± 0.5 (n = 3) |  |
| Example 7A | 1.5 ± 0.3 (n = 3) |  |
| Example 7B | 1.5 ± 0.4 (n = 3) |  |
| Zileuton | 0.5 ± 0.3 (n = 2) |  |

TABLE 4

Plasma DPLTD Blood

| Compound | $LTB_4$ | $TxB_2$ |
|---|---|---|
| Compound A | 0.5 (n = 2) | 4.9 (n = 2) |
| Compound B | 0.8 (n = 2) | 3.3 (n = 2) |
| Example 2 | 0.2 ± 0.1 (n = 7) | 4.9 ± 2.4 (n = 6) |
| Example 3 | 0.2 (n = 2) | 1.4 (n = 2) |
| Example 1 | 2.2 ± .4 (n = 3) | 2.4 ± 1.2 (n = 3) |
| Compound C | 1.5 ± 0.4 (n = 4) | 2.0 ± 0.6 (n = 4) |
| Compound D | 1.6 (n = 2) | >9.8 (n = 2) |

We claim:

1. A compound of the of formula II

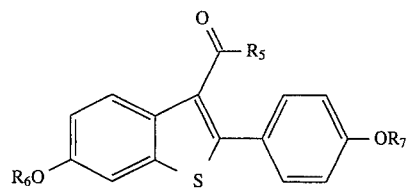

wherein $R_6$ and $R_7$ are hydrogen or $C_1$–$C_6$ alkyl, $R_5$ is naphthyl, substituted naphhyl, or phenyl substituted one to three times with $C_1$–$C_6$ alkoxy, $C_1$–$C_6$ alkyl, phenyl, or hydroxy; with the proviso that if $R_5$ is phenyl monosubstituted with hydroxy or $C_1$–$C_6$ alkoxy, then the phenyl must be further substituted once or twice with $C_1$–$C_6$ alkoxy, $C_1$–$C_6$ alkyl, phenyl, or hydroxy, and pharmaceutically acceptable salts thereof.

2. The compound of claim 1 wherein $R_6$ and $R_7$ are both hydrogen.

3. The compound of claim 2 wherein $R_5$ is naphthyl, substituted naphthyl, (p-phenyl)phenyl, dimethoxyphenyl, trimethoxyphenyl, p-t-butylphenyl, p-methylphenyl or m-methylphenyl.

4. The compound of claim 1 wherein said compound is selected from 6-hydroxyphenyl-2-(p-hydroxyphenyl)-(benzo(B)thien-3-yl) (p-phenyl)phenyl methanone;

6-hydroxyphenyl -2-(p-hydroxyphenyl)-(benzo(B)thien-3-yl) (a6-hydroxyphenyl-2-(p-hydroxyphenyl) -(benzo(B)thien-3-yl) (p-phenyl)phenyl methanone;

6-hydroxyphenyl-2-(p-hydroxyphenyl)-(benzo(B)thien-3-yl) (a-napthyl) methanone;

6-hydroxyphenyl-2-(p-hydroxyphenyl)-(benzo(B)thien-3-yl) (β-napthyl) methanone;

6-methoxyphenyl-2-(p-methoxyphenyl)-[(benzo(b)thien-3-yl)](benzo(B)thien-3-yl) (4-hydroxy-3,5-dimethoxyphenyl)methanone;

6-methoxyphenyl-2-(p-methoxyphenyl)-[(benzo(b)thien-3-yl)](benzo(B)thien-3-yl) (3,4,5-trimethoxypheyl)methanone;

6-hydroxyphenyl-2-(p-hydroxyphenyl)-[(benzo(b)thien-3-yl)](benzo(B)thien3-yl) (p-t-butylphenyl) methanone;

6-hydroxyphenyl-2-(p-hydroxyphenyl)-(benzo(B)thienyl-3-yl) (p-methylphenyl) methanone;

6-hydroxyphenyl-2-(p-hydroxyphenyl)-(benzo(B)thienyl-3-yl) (m-methylphenyl) methanone; or 6-hydroxyphenyl-2-(p-hydroxyphenyl)-(benzo(B)thien-3-yl) (m-hydroxyphenyl)methanone; and acceptable salts thereof.

* * * * *

UNITED STATES PATENT AND TRADEMARK OFFICE
CERTIFICATE OF CORRECTION

PATENT NO. : 5,532,382

DATED : July 2, 1996

INVENTOR(S) : Donald G. Carlson, et al.

It is certified that error appears in the above-identified patent and that said Letters Patent is hereby corrected as shown below:

Column 4, line 39, replace the phrase "6-hydroxyphenyl" with the phrase -- 6-hydroxy --.

Column 4, line 63, replace the phrase "6-hydroxyphenyl" with the phrase -- 6-hydroxy --.

Column 5, line 6, replace the phrase "6-hydroxyphenyl" with the phrase -- 6-hydroxy --.

Column 5, line 20, replace the phrase "6-hydroxyphenyl" with the phrase -- 6-hydroxy --.

Column 5, line 46, replace the phrase "X1 X506" with the phrase -- X1 X5006 --.

Column 5, line 57, replace the phrase "6-hydroxyphenyl" with the phrase -- 6-hydroxy --.

Column 6, line 3, replace the phrase "6-hydroxyphenyl" with the phrase -- 6-hydroxy --.

Column 6, line 17, replace the phrase "6-methoxyphenyl" with the phrase -- 6-methoxy --.

Column 6, line 21, replace the phrase "6-methoxyphenyl" with the phrase -- 6-methoxy --.

Column 6, line 38 replace the phrase "6-hydroxyphenyl" with the phrase -- 6-hydroxy --.

Column 6, line 45, replace the term "6.2." with the term -- 6.2.3. --

Column 6, line 54, replace the phrase "6-hydroxyphenyl" with the phrase -- 6-hydroxy --.

Column 7, line 3, replace the phrase "6-hydroxyphenyl" with the phrase -- 6-hydroxy --.

UNITED STATES PATENT AND TRADEMARK OFFICE
CERTIFICATE OF CORRECTION

PATENT NO. : 5,532,382
DATED : July 2, 1996
INVENTOR(S) : Donald G. Carlson, et al.

It is certified that error appears in the above-identified patent and that said Letters Patent is hereby corrected as shown below:

Column 7, line 10, replace the term "C 74.20/14.46" with the term -- C 74.20/74.46 --

Column 7, line 19, replace the phrase "6-hydroxyphenyl" with the phrase -- 6-hydroxy --.

Column 7, line 27, replace the phrase "400 mgs yield)" with the phrase -- 400 mgs (45% yield) --

Column 11, line 8, insert immediately preceding the phrase "for cPLA$_2$" the following phrase -- to a final concentration of 41 mg/ml. Samples to be assayed --

Column 13, line 6, replace the term "Elate" with the term -- plate --

Column 14, line 66, replace the phrase "6-hydroxyphenyl" with the phrase -- 6-hydroxy --.

Column 15, line 1, replace the phrase "6-hydroxyphenyl" with the phrase -- 6-hydroxy --.

Column 15, line 4, replace the phrase "6-hydroxyphenyl" with the phrase -- 6-hydroxy --.

Column 15, line 6, replace the phrase "6-hydroxyphenyl" with the phrase -- 6-hydroxy --.

Column 15, line 8, replace the phrase "6-methoxyphenyl" with the phrase -- 6-methoxy --.

Column 15, line 11, replace the phrase "6-methoxyphenyl" with the phrase -- 6-methoxy --.

Column 16, line 1, replace the phrase "6-hydroxyphenyl" with the phrase -- 6-hydroxy --.

UNITED STATES PATENT AND TRADEMARK OFFICE
CERTIFICATE OF CORRECTION

PATENT NO. : 5,532,382
DATED : July 2, 1996
INVENTOR(S) : Donald G. Carlson, et al.

It is certified that error appears in the above-identified patent and that said Letters Patent is hereby corrected as shown below:

Column 16, line 3, replace the phrase "6-hydroxyphenyl" with the phrase -- 6-hydroxy --.

Column 16, line 5 replace the phrase "6-hydroxyphenyl" with the phrase -- 6-hydroxy --.

Column 16, line 7 replace the phrase "6-hydroxyphenyl" with the phrase -- 6-hydroxy --.

Signed and Sealed this

Twenty-fourth Day of August, 1999

Q. TODD DICKINSON

*Attest:*

*Attesting Officer*  *Acting Commissioner of Patents and Trademarks*